Patent Number: 4,774,260
… Date of Patent: * Sep. 27, 1988

[54] NOVEL BENZOYLUREA PESTICIDES

[75] Inventors: Wilhelm Sirrenberg, Sprockhoevel; Erich Klauke, Odenthal; Benedikt Becker, Mettmann; Ingomar Krehan, Cologne; Wilhelm Stendel, Wuppertal, all of Fed. Rep. of Germany

[73] Assignee: Bayer Aktiengesellschaft, Leverkusen, Fed. Rep. of Germany

[*] Notice: The portion of the term of this patent subsequent to Aug. 6, 2002 has been disclaimed.

[21] Appl. No.: 843,449

[22] Filed: Mar. 24, 1986

Related U.S. Application Data

[63] Continuation of Ser. No. 587,088, Mar. 7, 1984, abandoned.

[30] Foreign Application Priority Data

Mar. 19, 1983 [DE] Fed. Rep. of Germany ....... 3309987
Nov. 15, 1983 [DE] Fed. Rep. of Germany ....... 3341276

[51] Int. Cl.$^4$ .................. C07C 157/12; C07C 127/22; A01N 47/34
[52] U.S. Cl. ..................... 514/594; 564/23; 564/44; 514/584
[58] Field of Search ............... 564/44, 23; 514/594, 514/584

[56] References Cited

U.S. PATENT DOCUMENTS 4,005,223  1/1977  Sirrenberg et al. ................. 564/44
4,533,676  8/1985  Sirrenberg et al. ............. 514/594 X

FOREIGN PATENT DOCUMENTS 57888   8/1982  European Pat. Off. .
74074   3/1983  European Pat. Off. .
93977   11/1983  European Pat. Off. .
92857   7/1981  Japan ................................. 564/44

OTHER PUBLICATIONS

Patent Abstracts of Japan, vol. 5, No. 75, 5/19/1981.

Primary Examiner—Glennon H. Hollrah
Assistant Examiner—Carolyn S. Greason
Attorney, Agent, or Firm—Sprung Horn Kramer & Woods

[57] ABSTRACT

1-Phenyl-3-benzoyl-(thio)ureas of the formula

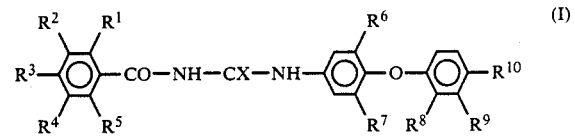

in which
X represents oxygen or sulphur,
$R^1$ represents hydrogen, halogen, nitro, alkyl or alkylthio,
$R^2$, $R^4$ and $R^5$ are identical or different and represent hydrogen or halogen,
$R^3$ represents hydrogen, halogen or nitro,
$R^6$ and $R^7$ are identical or different and represent hydrogen, halogen or alkyl,
$R^8$ and $R^9$ are identical or different and represent hydrogen or halogen and
$R^{10}$ represents halogenoalkylthio or halogenoalkoxy, with certain exclusions, which possess insecticidal and acaricidal activity.

11 Claims, No Drawings

NOVEL BENZOYLUREA PESTICIDES

This is a continuation of application Ser. No. 587,088, filed Mar. 7, 1984, now abandoned.

The present invention relates to new substituted 1-phenyl-3-benzoyl-(thio)ureas, several processes for their preparation and their use as pest-combating agents, in particular as insecticides and acaricides.

It is already known that certain benzoylureas possess insecticidal properties (see for example European Pat. No. 0,057,888).

The new substituted 1-phenyl-3-benzoyl-(thio)ureas of the formula (I)

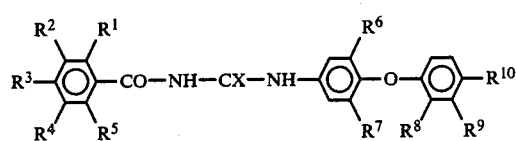

have been found, in which
X represents oxygen or sulphur,
$R^1$ represents hydrogen, halogen, nitro, alkyl or alkylthio,
$R^2$, $R^4$ and $R^5$ are identical or different and represent hydrogen or halogen,
$R^3$ represents hydrogen, halogen or nitro,
$R^6$ and $R^7$ are identical or different and represent hydrogen, halogen or alkyl,
$R^8$ and $R^9$ are identical or different and represent hydrogen or halogen and
$R^{10}$ represents halogenoalkylthio or halogenoalkoxy, and (1) if X represents oxygen and
$R^2$, $R^3$, $R^4$, $R^6$, $R^8$ and $R^9$ represent hydrogen and
$R^7$ represents hydrogen or halogen and
(a) $R^1$ and $R^5$ both represent halogen or
(b) $R^1$ represents halogen, nitro or alkyl and
$R^5$ represents hydrogen,
in these cases the radical
$R^{10}$ always denotes halogenoalkylthio, and
(2) if X represents oxygen or sulphur and
$R^6$ represents chlorine and
$R^8$ represents hydrogen or chlorine and
$R^9$ represents hydrogen and
$R^{10}$ represents halogenoalkylthio or halogenoalkoxy and
(a) $R^1$ and $R^3$ represent halogen and $R^2$, $R^4$ and $R^5$ represent hydrogen or
(b) $R^5$ and $R^3$ represent halogen and $R^1$, $R^2$ and $R^4$ represent hydrogen or
(c) $R^1$ and $R^4$ represent halogen and $R^2$, $R^3$ and $R^5$ represent hydrogen or
(d) $R^2$ and $R^5$ represent halogen and $R^1$, $R^3$ and $R^4$ represent hydrogen,
in these cases the radical
$R^7$ always denotes hydrogen or alkyl.

These new compounds have powerful biological properties, in particular insecticidal properties, which make it possible to use them as pest-combating agents, in particular as insecticides and acaricides.

Furthermore, it has been found that the new substituted 1-phenyl-3-benzoyl-(thio)ureas of the formula (I) are obtained by a process in which
(a) substituted anilines of the formula (II)

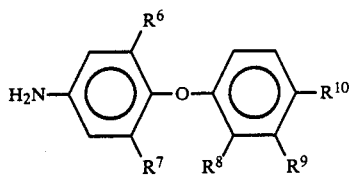

in which
$R^6$, $R^7$, $R^8$, $R^9$ and $R^{10}$ have the meanings given above,
are reacted with benzoyl-iso(thio)cyanates of the formula III

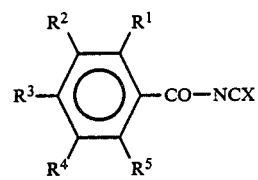

in which
X, $R^1$, $R^2$, $R^3$, $R^4$ and $R^5$ have the meanings given above,
if appropriate in the presence of a diluent, or
(b) substituted phenyl-iso(thio)cyanates of the formula (IV)

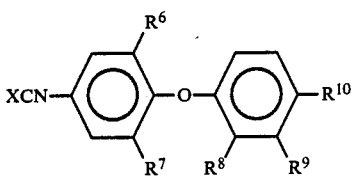

in which
X, $R^6$, $R^7$, $R^8$, $R^9$ and $R^{10}$ have the meanings given above,
are reacted with benzoic acid amides of the formula (V)

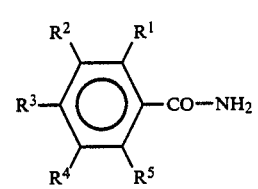

in which
$R^1$, $R^2$, $R^3$, $R^4$ and $R^5$ have the meanings given above, if appropriate in the presence of a catalyst and, if appropriate, in the presence of a diluent.

Alkyl $R^1$, $R^6$ and $R^7$ and alkylthio $R^1$ contain, in the alkyl part, straight-chain or branched alkyl having 1 to 12, preferably 1 to 6, in particular 1 to 4, carbon atoms. Methyl, ethyl, n-propyl, i-propyl, n-butyl, i-butyl, sec.-butyl, tert.-butyl, methylthio, ethylthio, n-propylthio, i-propylthio, n-butylthio, i-butylthio, sec.-butylthio and tert.-butylthio may be mentioned as examples.

Halogenoalkylthio and halogenoalkoxy $R^{10}$ each contain, in the alkyl part, straight-chain or branched alkyl having 1 to 6, preferably 1 to 4, in particular 1 or 2, carbon atoms and preferably 1 to 6, in particular 1 to 4, halogen atoms, the halogen atoms being identical or different and preferred halogen atoms being fluorine, chlorine or bromine, in particular fluorine. Trifluoromethylthio, chlorodifluoromethylthio, trifluoroethylthio, chlorotrifluoroethylthio, tetrafluoroethylthio, trifluoromethoxy, difluoromethoxy, tetrafluoroethoxy, chlorotrifluoroethoxy and bromotrifluoroethoxy may be mentioned as examples.

Where not stated otherwise, halogen denotes fluorine, chlorine, bromine and iodine, preferably fluorine, chlorine and bromine.

X preferably represents oxygen.

The new compounds of the formula (I) have properties which make it possible to use them as pest-combating agents; in particular, they are distinguished by an excellent insecticidal and acaricidal activity.

The invention preferably relates to new compounds of the formula (I), in which

X represents sulphur or oxygen, $R^1$ represents hydrogen, halogen, nitro or a radical from the series comprising $C_1$–$C_6$-alkyl and $C_1$–$C_6$-alkylthio, $R^2$, $R^4$ and $R^5$ are identical or different and represent hydrogen or halogen, $R^3$ represents hydrogen, halogen or nitro, $R^6$ and $R^7$ are identical or different and represent hydrogen, halogen or a $C_1$–$C_6$-radical, $R^8$ and $R^9$ are identical or different and represent hydrogen or halogen and $R^{10}$ represents halogenoalkylthio or halogenoalkoxy having 1 to 4 carbon atoms and 1 to 4 halogen atoms (preferably chlorodifluoromethylthio, trifluoromethylthio, chlorodifluoromethoxy or trifluoromethoxy), and (1) if X represents oxygen and
$R^2$, $R^3$, $R^4$, $R^6$, $R^8$ and $R^9$ represent hydrogen and
$R^7$ represents hydrogen or halogen and
(a) $R^1$ and $R^5$ both represent halogen or
(b) $R^1$ represents halogen, nitro or $C_1$–$C_6$-alkyl and $R^5$ represents hydrogen,
in these cases the radical
$R^{10}$ always denotes $C_1$–$C_4$-halogenoalkylthio, and (2) if X represents oxygen or sulphur and
$R^6$ represents chlorine and
$R^8$ represents hydrogen or chlorine and
$R^9$ represents hydrogen and
$R^{10}$ represents $C_1$–$C_4$-halogenoalkylthio or $C_1$–$C_4$-halogenoalkoxy and
(a) $R^1$ and $R^3$ represent halogen and $R^2$, $R^4$ and $R^5$ represent hydrogen or
(b) $R^5$ and $R^3$ represent halogen and $R^1$, $R^2$ and $R^4$ represent hydrogen or
(c) $R^1$ and $R^4$ represent halogen and $R^2$, $R^3$ and $R^5$ represent hydrogen or
(d) $R^2$ and $R^5$ represent halogen and $R^1$, $R^3$ and $R^4$ represent hydrogen,
in these cases the radical
$R^7$ always denotes hydrogen or $C_1$–$C_6$-alkyl.

In each case, halogen represents fluorine, chlorine, bromine and/or iodine, preferably fluorine, chlorine and/or bromine.

Particularly preferred compounds are those of the formula (I) in which

X represents oxygen or sulphur, $R^1$ represents hydrogen, fluorine, chlorine, bromine, nitro, methyl, ethyl, n-propyl, i-propyl, n-butyl, i-butyl, sec.-butyl, tert.-butyl, methylthio, ethylthio, n-propylthio, i-propylthio, n-butylthio, i-butylthio, sec.-butylthio or tert.-butylthio, $R^2$, $R^4$ and $R^5$ are identical or different and represnt hydrogen, fluorine, chlorine or bromine, $R^3$ represents hydrogen, fluorine, chlorine, bromine or nitro, $R^6$ and $R^7$ are identical or different and represent hydrogen, fluorine, chlorine, bromine, methyl, ethyl, n-propyl, i-propyl, n-butyl, i-butyl, sec.-butyl or tert.-butyl, $R^8$ and $R^9$ are identical or different and represent hydrogen, fluorine, chlorine or bromine and $R^{10}$ represents trifluoromethylthio or trifluoromethoxy, and (1) if X represents oxygen and
$R^2$, $R^3$, $R^4$, $R^6$, $R^8$ and $R^9$ represent hydrogen and
$R^7$ represents hydrogen, fluorine, chlorine or bromine and
(a) $R^1$ and $R^5$ both represent fluorine, chlorine and/or bromine or
(b) $R^1$ represents fluorine, chlorine, bromine, nitro or the abovementioned alkyl radicals and $R^5$ represents hydrogen,
in these cases the radical
$R^{10}$ always denotes trifluoromethylthio, and (2) if X represents oxygen or sulphur and
$R^6$ represents chlorine and
$R^8$ represents hydrogen or chlorine and
$R^9$ represents hydrogen and
$R^{10}$ represents trifluoromethylthio or trifluoromethoxy and
(a) $R^1$ and $R^3$ represent fluorine, chlorine or bromine and $R^2$, $R^4$ and $R^5$ represent hydrogen or
(b) $R^5$ and $R^3$ represent fluorine, chlorine or bromine and $R^1$, $R^2$ and $R^4$ represent hydrogen or
(c) $R^1$ and $R^4$ represent fluorine, chlorine or bromine and $R^2$, $R^3$ and $R^5$ represent hydrogen or
(d) $R^2$ and $R^5$ represent fluorine, chlorine or bromine and $R^1$, $R^3$ and $R^4$ represent hydrogen, in these cases the radical
$R^7$ always denotes hydrogen or the abovementioned alkyl radicals.

Very particularly preferred compounds are those of the formula (I), in which

X represents oxygen, $R^1$ represents hydrogen, fluorine, chlorine, bromine, nitro, methyl or methylthio, $R^2$, $R^4$ and $R^5$ represent hydrogen, fluorine, chlorine or bromine, $R^3$ represents hydrogen, fluorine, chlorine or nitro, $R^6$ and $R^7$ are identical or different and represent hydrogen, chlorine or methyl, $R^8$ and $R^9$ are identical or different and represent hydrogen, fluorine or chlorine and $R^{10}$ represents trifluoromethylthio or trifluoromethoxy, and (1) if $R^2$, $R^3$, $R^4$, $R^6$, $R^8$ and $R^9$ represent hydrogen and
$R^7$ represents hydrogen or chlorine and
(a) $R^1$ and $R^5$ both represent fluorine, chlorine and/or bromine or
(b) $R^1$ represents fluorine, chlorine, bromine, nitro or methyl and $R^5$ represents hydrogen, in these cases the radical
$R^{10}$ always denotes trifluoromethylthio, and (2) if $R^6$ represents chlorine and
$R^8$ represents hydrogen or chlorine and
$R^9$ represents hydrogen and
$R^{10}$ represents trifluoromethylthio or trifluoromethoxy and (a) $R^1$ and $R^3$ represent fluorine, chlorine and/or bromine and $R^2$, $R^4$ and $R^5$ represent hydrogen or (b) $R^5$ and $R^3$ represent fluorine, chlorine and/or bromine and $R^1$, $R^2$ and $R^4$ represent hydrogen or (c) $R^1$ and $R^4$ represent fluorine, chlorine and/or bromine and $R^2$, $R^3$ and $R^5$ represent hydrogen or (d) $R^2$ and $R^5$ represent fluorine, chlorine and/or bromine and $R^1$, $R^3$ and $R^4$ represent hydrogen, in these cases the radical
$R^7$ always denotes hydrogen or methyl.

If 4-(2-chloro-4-trifluoromethoxy-phenoxy)-3-methyl-aniline and 2,6-difluorobenzoyl isocyanate are used as starting materials according to process variant (a), the course of the reaction can be represented by the following equation:

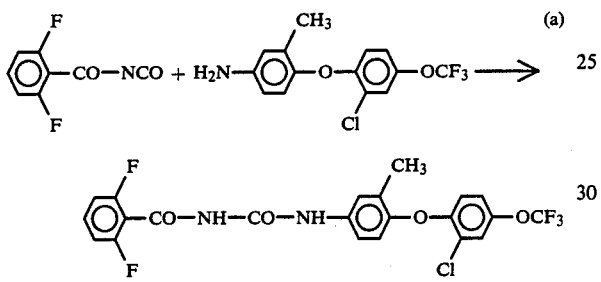

If 4-(2-chloro-4-trifluoromethoxy-phenoxy)-3-methyl-phenylisothiocyanate and 2,6-difluoro-benzamide are used as starting materials according to process variant (b), the course of the reaction can be represented by the following equation:

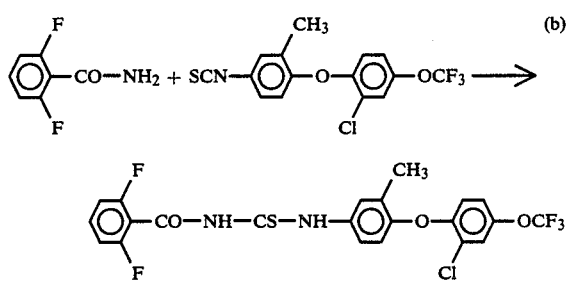

The following may be mentioned as examples of the compounds of the formula (II):

TABLE 1

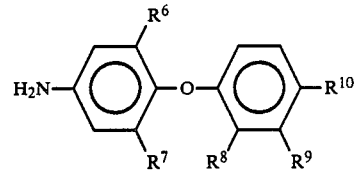

| $R^6$ | $R^7$ | $R^8$ | $R^9$ | $R^{10}$ |
|---|---|---|---|---|
| H | H | H | H | OCF$_3$ |
| Cl | H | H | H | OCF$_3$ |
| Cl | Cl | H | H | OCF$_3$ |
| H | Cl | Cl | H | OCF$_3$ |
| H | H | Cl | Cl | OCF$_3$ |

TABLE 1-continued

| $R^6$ | $R^7$ | $R^8$ | $R^9$ | $R^{10}$ |
|---|---|---|---|---|
| Cl | H | H | Cl | OCF$_3$ |
| H | H | Cl | H | OCF$_3$ |
| H | H | H | Cl | OCF$_3$ |
| Cl | Cl | Cl | H | OCF$_3$ |
| Cl | Cl | H | Cl | OCF$_3$ |
| Cl | H | Cl | Cl | OCF$_3$ |
| Cl | Cl | Cl | Cl | OCF$_3$ |
| CH$_3$ | H | H | H | OCF$_3$ |
| CH$_3$ | Cl | H | H | OCF$_3$ |
| CH$_3$ | H | Cl | H | OCF$_3$ |
| CH$_3$ | H | H | Cl | OCF$_3$ |
| CH$_3$ | H | Cl | Cl | OCF$_3$ |
| CH$_3$ | Cl | Cl | H | OCF$_3$ |
| CH$_3$ | Cl | H | Cl | OCF$_3$ |
| CH$_3$ | Cl | Cl | Cl | OCF$_3$ |
| CH$_3$ | CH$_3$ | H | H | OCF$_3$ |
| CH$_3$ | CH$_3$ | Cl | H | OCF$_3$ |
| CH$_3$ | CH$_3$ | H | Cl | OCF$_3$ |
| CH$_3$ | CH$_3$ | Cl | Cl | OCF$_3$ |
| H | H | H | H | SCF$_3$ |
| Cl | H | H | H | SCF$_3$ |
| Cl | Cl | H | H | SCF$_3$ |
| H | Cl | Cl | H | SCF$_3$ |
| H | H | Cl | Cl | SCF$_3$ |
| Cl | H | H | Cl | SCF$_3$ |
| Cl | H | Cl | H | SCF$_3$ |
| H | H | Cl | H | SCF$_3$ |
| H | H | H | Cl | SCF$_3$ |
| Cl | Cl | Cl | H | SCF$_3$ |
| Cl | Cl | H | Cl | SCF$_3$ |
| Cl | H | Cl | Cl | SCF$_3$ |
| Cl | Cl | Cl | Cl | SCF$_3$ |
| CH$_3$ | H | H | H | SCF$_3$ |
| CH$_3$ | Cl | H | H | SCF$_3$ |
| CH$_3$ | H | Cl | H | SCF$_3$ |
| CH$_3$ | H | H | Cl | SCF$_3$ |
| CH$_3$ | H | Cl | Cl | SCF$_3$ |
| CH$_3$ | Cl | Cl | H | SCF$_3$ |
| CH$_3$ | Cl | H | Cl | SCF$_3$ |
| CH$_3$ | Cl | Cl | Cl | SCF$_3$ |
| CH$_3$ | CH$_3$ | H | H | SCF$_3$ |
| CH$_3$ | CH$_3$ | Cl | H | SCF$_3$ |
| CH$_3$ | CH$_3$ | H | Cl | SCF$_3$ |
| CH$_3$ | CH$_3$ | Cl | Cl | SCF$_3$ |

Substituted anilines of the formula (II) which are to be used as starting materials are known and can be prepared by processes and methods which are known from the literature (see DE-OS (German Published Specification) No. 3,217,619, DE-OS (German Published Specification) No. 3,217,620 and European Pat. No. 0,057,588); the amino group can be converted to the isocyanate or iso-thio-cyanate group by customary processes, for example by reaction with phosgene or thiophosgene, whereby the corresponding substituted phenyl iso(thio)cyanates of the formula (IV) are obtained.

The corresponding isocyanates or iso-thio-cyanates of the substituted anilines of the formula (II) which are listed in Table 1 may be mentioned as examples of the compounds of the formula (IV).

The following may be mentioned as examples of the compounds of the formula (III): 2-fluoro-, 2-chloro-, 2-bromo-, 2-nitro-, 2-methyl-, 2-methylthio-, 2,6-difluoro-, 2,6-dichloro-, 2-chloro-6-fluoro-, 2-chloro-4-nitro-, 3,4-difluoro-, 3,4-dichloro-, 2,3,6-trichloro-, 4- fluoro-, 4-chloro-, 4-bromo- and 4-nitrobenzoyl isocyanate or -benzoyl isothiocyanate.

The starting compounds of the formula (III) are known.

The following may be mentioned as examples of the compounds of the formula (V): 2-fluoro-, 2-chloro-, 2-bromo-, 2-nitro-, 2-methyl-, 2-methylthio-, 2,6-difluoro-, 2,6-dichloro-, 2-chloro-6-fluoro-, 2-chloro-4-nitro-, 3,4-difluoro-, 3,4-dichloro-, 2,3,6-trichloro-, 4-fluoro-, 4-chloro-, 4-bromo- and 4-nitrobenzoic acid amide.

The compounds of the formula (V) are known.

Suitable diluents are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylenesulphone.

Catalysts used for the reaction according to process variant (b) are preferably tertiary amines, such as triethylamine and 1,4-diazabicyclo[2,2,2]octane, and organic tin compounds, such as, for example, dibutyl-tin dilaurate.

The reaction temperature can be varied within a relatively wide range. In general, process variant (a) is carried out at between 20° and 180° C., preferably between 40° and 120° C., and process variant (b) is carried out between 20° and 200° C., preferably between 60° and 190° C. The process variants according to the invention are carried out in general under atmospheric pressure.

For carrying out the process variants according to the invention, the starting materials are usually employed in about equimolar amounts. An excess of one or the other of the reactants has no substantial advantages.

The reaction products are worked up by customary methods, for example by filtering off the precipitated product under suction or by extracting the undesired byproducts from the reaction mixture. They are characterized by their melting point.

The active compounds are well tolerated by plants, have a favorable level of toxicity to warm-blooded animals, and are suitable for combating animal pests, especially insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria -migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and *Tetranychus spp..*

The active compounds can be converted to the customary formulations, such as solutions, emulsions, suspensions, powders, foams, pastes, granule, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as koalins, clays, talc, chalk, quartz, attapulgite, montmorrillonite or diatomaceous earth, and ground synthetic minerals, such as highly dispersed silicic acid, alumina and silicates; as solid carriers for granules there are suitable: for example crushed and fractionated rocks such as calcite, marble, pumice, sepiolite and dolomite, as well as synthetic granules of inorganic and organic meals, and granules of organic material such as sawdust, coconut shells, oorn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of animal husbandry and livestock breeding, it being possible to achieve better results, for example higher milk yields, higher weight, finer animal skin, longer life span, etc., by combating the pests.

The active compounds according to the invention are used in a known manner in these fields, such as by external application, for example in the form of dipping, spraying, pouring on and spotting on, and dusting, and by oral administration, for example via the feed or drinking water, for example in the form of tablets, capsules, drinks and granules.

The preparation examples which follow are intended to illustrate the preparation of the compounds according to the invention:

EXAMPLE 1

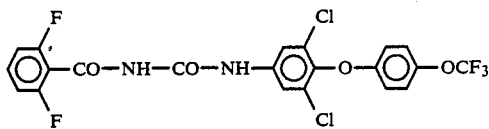

(Process variant a)

3.66 g (0.02 mole) of 2,6-difluorobenzoyl isocyanate in 10 ml of toluene are added to a solution of 6.76 g (0.02 mole) of 3,5-dichloro-4-(4-trifluoromethoxy-phenoxy)-aniline in 60 ml of dry toluene at 60° C. The mixture is then stirred for one hour at 80° C. After it has been cooled to 20° C., the product is filtered off under suction and dried.

9 g (86.5% of theory) of 1-(2,6-difluorobenzoyl)-3-[3,5-dichloro-4-(4-trifluoromethoxy-phenoxy)-phenyl]-urea of melting point m.p. 194° C. are obtained.

EXAMPLE 2

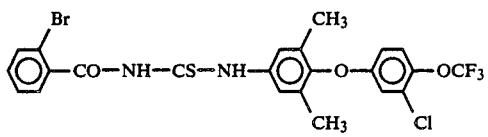

(Process variant b)

2.42 g (0.01 mole) of 2-bromobenzoyl isothiocyanate in 10 ml of toluene are added to a solution of 3.32 g (0.01 mole) of 3,5-dimethyl-4-(3-chloro-4-trifluoromethoxy-phenoxy)-aniline in 50 ml of dry toluene at 60° C. The mixture is then stirred for 30 minutes at 80° C. and then evaporated down to a volume of 20 ml. The precipitate is filtered off under suction and dried.

5.1 g (89% of theory) of 1-(2-bromobenzoyl)-3-[3,5-dimethyl-4-(3-chloro-4-trifluoromethoxy-phenoxy)-phenyl]-urea of melting point m.p.: 167° C. are obtained.

The following compounds of the formula (I) were prepared analogously to Examples 1 or 2, or process variant (a) or (b):

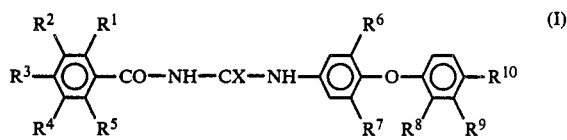

TABLE 2

| Ex. No. | $R^1$ | $R^2$ | $R^3$ | $R^4$ | $R^5$ | $R^6$ | $R^7$ | $R^8$ | $R^9$ | $R^{10}$ | x | m.p. °C. |
|---|---|---|---|---|---|---|---|---|---|---|---|---|
| 3 | Cl | H | H | H | H | Cl | Cl | H | H | $OCF_3$ | O | 194 |
| 4 | Cl | H | H | H | F | Cl | Cl | H | H | $OCF_3$ | O | 193 |
| 5 | Br | H | H | H | H | Cl | Cl | H | H | $SCF_3$ | O | 199 |
| 6 | Cl | H | H | H | H | Cl | Cl | H | H | $SCF_3$ | O | 198 |
| 7 | F | H | H | H | F | Cl | Cl | H | H | $SCF_3$ | O | 215 |
| 8 | Cl | H | H | H | Cl | Cl | Cl | H | H | $SCF_3$ | O | 226 |
| 9 | Cl | H | H | H | F | Cl | Cl | H | H | $SCF_3$ | O | 226 |
| 10 | F | H | H | H | F | Cl | Cl | Cl | H | $OCF_3$ | O | 167 |
| 11 | Cl | H | H | H | F | Cl | Cl | Cl | H | $OCF_3$ | O | 154 |
| 12 | Cl | H | H | H | H | Cl | Cl | Cl | H | $OCF_3$ | O | 178 |
| 13 | F | H | H | H | F | Cl | Cl | Cl | H | $OCF_3$ | S | 170 |
| 14 | Br | H | H | H | H | Cl | Cl | Cl | H | $OCF_3$ | S | 151 |
| 15 | Cl | H | H | H | F | Cl | Cl | Cl | H | $OCF_3$ | S | 182 |
| 16 | $NO_2$ | H | H | H | H | Cl | Cl | H | H | $OCF_3$ | O | 202 |
| 17 | $SCH_3$ | H | H | H | H | Cl | Cl | H | H | $OCF_3$ | O | 181 |
| 18 | H | H | Cl | H | H | Cl | Cl | Cl | H | $OCF_3$ | O | 232 |
| 19 | Cl | H | $NO_2$ | H | H | Cl | Cl | Cl | H | $OCF_3$ | O | 230 |
| 20 | H | Cl | Cl | H | H | Cl | Cl | Cl | H | $OCF_3$ | O | 128 |
| 21 | Br | H | H | H | H | Cl | Cl | Cl | H | $OCF_3$ | O | 171 |
| 22 | $CH_3$ | H | H | H | H | Cl | Cl | Cl | H | $OCF_3$ | O | 188 |
| 23 | Cl | H | H | H | Cl | Cl | Cl | Cl | H | $OCF_3$ | O | 203 |
| 24 | $CH_3$ | H | H | H | H | Cl | Cl | H | H | $OCF_3$ | O | 206 |
| 25 | Br | H | H | H | H | Cl | Cl | H | H | $OCF_3$ | O | 200 |
| 26 | Cl | H | H | H | Cl | Cl | Cl | H | H | $OCF_3$ | S | 194 |
| 27 | Cl | H | H | H | F | Cl | Cl | H | H | $OCF_3$ | S | 152 |
| 28 | F | H | H | H | F | Cl | Cl | H | H | $OCF_3$ | S | 145 |
| 29 | Cl | H | H | H | Cl | H | H | H | H | $OCF_3$ | S | 154 |
| 30 | F | H | H | H | F | H | H | H | H | $OCF_3$ | S | 139 |
| 31 | Cl | H | H | H | F | Cl | H | H | H | $OCF_3$ | S | 121 |
| 32 | Cl | H | H | H | H | H | H | Cl | H | $OCF_3$ | O | 154 |
| 33 | F | H | H | H | F | H | H | Cl | H | $OCF_3$ | O | 162 |
| 34 | Br | H | H | H | H | H | H | Cl | H | $OCF_3$ | O | 167 |
| 35 | Cl | H | H | H | Cl | H | H | Cl | H | $OCF_3$ | S | 156 |
| 36 | Cl | H | H | H | F | H | H | Cl | H | $OCF_3$ | S | 148 |
| 37 | Cl | H | H | H | H | Cl | H | Cl | H | $OCF_3$ | O | 151 |
| 38 | F | H | H | H | F | Cl | H | Cl | H | $OCF_3$ | O | 156 |
| 39 | Cl | H | H | H | Cl | Cl | H | Cl | H | $OCF_3$ | S | 143 |
| 40 | Cl | H | H | H | Cl | Cl | H | Cl | H | $OCF_3$ | O | 188 |
| 41 | Cl | H | H | H | H | Cl | Cl | H | Cl | $OCF_3$ | O | 200 |
| 42 | Cl | H | H | H | H | Cl | Cl | Cl | H | $SCF_3$ | O | 207 |
| 43 | F | H | H | H | F | Cl | Cl | Cl | H | $SCF_3$ | O | 216 |
| 44 | F | H | H | H | F | Cl | Cl | H | Cl | $OCF_3$ | O | 196 |
| 45 | Cl | H | H | H | F | Cl | Cl | H | H | $SCF_3$ | S | 166 |
| 46 | $CH_3$ | H | H | H | H | Cl | Cl | Cl | H | $SCF_3$ | O | 207 |
| 47 | Cl | H | H | H | F | Cl | Cl | H | Cl | $OCF_3$ | S | 161 |
| 48 | Br | H | H | H | H | Cl | Cl | H | Cl | $OCF_3$ | S | 154 |
| 49 | Br | H | H | H | H | Cl | Cl | Cl | H | $SCF_3$ | O | 204 |
| 50 | Br | H | H | H | H | Cl | Cl | H | Cl | $OCF_3$ | O | 180 |
| 51 | $CH_3$ | H | H | H | H | Cl | Cl | H | Cl | $OCF_3$ | O | 207 |
| 52 | Cl | H | H | H | Cl | Cl | Cl | H | H | $SCF_3$ | O | 205 |
| 53 | Cl | H | H | H | Cl | Cl | Cl | Cl | H | $OCF_3$ | O | 220 |
| 54 | Cl | H | H | H | Cl | $CH_3$ | $CH_3$ | H | Cl | $OCF_3$ | O | 191-192 |
| 55 | Cl | H | H | H | H | $CH_3$ | $CH_3$ | H | Cl | $OCF_3$ | O | 174-175 |
| 56 | Cl | H | H | H | F | $CH_3$ | $CH_3$ | H | Cl | $OCF_3$ | O | 172-173 |
| 57 | F | H | H | H | F | $CH_3$ | $CH_3$ | H | Cl | $OCF_3$ | O | 182-183 |
| 58 | Cl | H | H | H | H | $CH_3$ | $CH_3$ | Cl | H | $OCF_3$ | O | 200-206 |
| 59 | Cl | H | H | H | H | $CH_3$ | $CH_3$ | H | H | $SCF_3$ | O | 201 |
| 60 | Cl | H | H | H | F | $CH_3$ | $CH_3$ | Cl | H | $OCF_3$ | O | 151 |
| 61 | F | H | H | H | F | $CH_3$ | $CH_3$ | H | H | $SCF_3$ | O | 200 |

TABLE 2-continued

| Ex. No. | R¹ | R² | R³ | R⁴ | R⁵ | R⁶ | R⁷ | R⁸ | R⁹ | R¹⁰ | x | m.p. °C. |
|---|---|---|---|---|---|---|---|---|---|---|---|---|
| 62 | F | F | F | F | F | Cl | Cl | Cl | H | OCF₃ | O | 196 |
| 63 | F | H | H | H | F | CH₃ | CH₃ | Cl | H | OCF₃ | O | 149 |
| 64 | Cl | H | H | H | F | CH₃ | CH₃ | Cl | H | OCF₃ | S | 155 |
| 65 | F | H | H | H | F | CH₃ | CH₃ | Cl | H | OCF₃ | S | 133 |

The examples which follow are intended to illustrate the biological activity of the compounds according to the invention.

EXAMPLE A

Plutella test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the compounds of Preparation Examples 1, 3, 4, 7, 10, 11, 12, 21, 22, 37, 38, 43, 44, 57, 58, 60, 61 and 63 showed a destruction of 100% after 7 days, for example at a concentration of 0.001%.

EXAMPLE B

Mosquito larvae test

Test insects: *Aedes aegypti* (2nd instar larvae)
Solvent: acetone: 99 parts by weight
Emulsifier: alkylaryl polyglycol ether: 1 part by weight To produce a suitable preparation of active compound, 2 parts by weight of active compound are dissolved in 1,000 parts by volume of the solvent, containing the amount of emulsifier stated above. The solution thus obtained is diluted with water to the desired lower concentrations.

The aqueous preparations of active compound of the desired concentration are filled into plastic vessels and 20 mosquito larvae (2nd instar larvae) are then placed in each vessel. The larvae are daily feeded.

After 1, 8 and 21 days, the degree of destruction in % is determined. 100% means that all the larvae (or puppae respectively) have been killed. 0% means that no larvae at all have been killed.

In this test, for example, the compound of preparation examples 38 and 63 showed a destruction of 100%, for example at a concentration of $10^{-4}$ ppm after 21 days.

EXAMPLE C

Test with parasitic fly larvae (*Lucilia cuprina*)

Solvent: 35 parts by weight of ethylene glycol monomethyl ether
Emulsifier: 35 parts by weight of nonylphenol polyglycol ether To produce a suitable preparation of active compound, 30 parts by weight of the active substance in question are mixed with the stated amount of solvent which contains the abovementioned proportion of emulsifier and the concentrate thus obtained is diluted with water to the desired concentration.

About 20 fly larvae (*Lucilia cuprina*) are introduced into a test tube which contains aboul 2 cm³ of horse muscle. 0.5 ml of the preparation of active compound is applied to this horse meat. After 24 hours, the degree of destruction in % is determined. 100% means that all of the larvae have been killed and 0% (control) means that none of the larvae have been killed.

In a trial for example with an active compound concentration of 1,000 ppm, for example the compounds of preparation examples (1) and (4) showed a destruction of 100%.

EXAMPLE D

Tetranychus test (resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, the compounds of preparation examples 2, 33, 37, 38, 43, 47, 55, 56, 57, 58, 60, 61 and 63 showed after 10 days a destruction of 98%, for example at a concentration of 0.1%.

It is understood that the specification and examples are illustrative but not limitative of the present invention and that other embodiments within the spirit and scope of the invention will suggest themselves to those skilled in the art.

We claim:

1. A 1-phenyl-3-benzoyl-(thio)urea of the formula in which
  X represents oxygen or sulphur,
  R¹ represents hydrogen, fluorine, chlorine or bromine, $R^5$ represents fluorine, chlorine or bromine,
$R^6$ represents hydrogen or methyl,
$R^8$ represents fluorine or chlorine, and
$R^9$ represents hydrogen or halogen.

2. An insecticidal or acaricidal composition comprising an insecticidally or acaricidally effective amount of a compound according to claim 1 in admixture with a diluent.

3. A method of killing insects or acarids which comprises administering to such insects or acarids an insecticidally or acaricidally effective amount of a compound according to claim 1.

4. A compound selected from the group consisting of 1-(2-chlorobenzoyl)-3-[3-chloro-4-(2-chloro-4-trifluoromethoxy-phenoxy)-phenyl]-urea of the formula

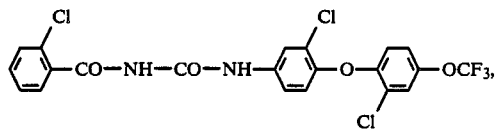

1-(2,6-difluorobenzoyl)-3-3-chloro-4-(2-chloro-4-trifluoromethoxy-phenoxy)-phenyl]-urea of the formula

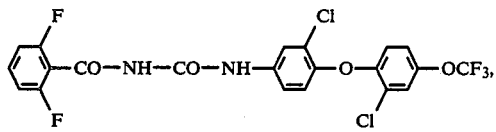

1(2,6-difluorobenzoyl)-3-3,5-dimethyl-4-(3-chloro-4-trifluoromethoxy-phenoxy)-phenyl]-urea of the

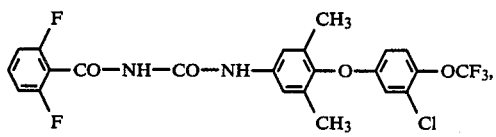

1-(2-chlorobenzoyl)-3-3,5-dimethyl-4-(2-chloro-4-trifluoromethoxy-phenoxy)-phenyl]-urea of the formula

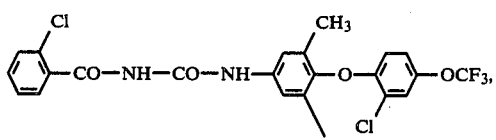

and
1-(2,6-difluorobenzoyl)-3-3,5-dimethyl-4-(2-chloro-4-trifluoromethoxy-phenoxy)-phenyl]-urea of the formula

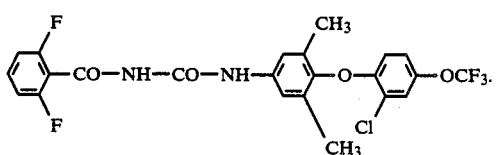

5. A compound according to claim 4, wherein such compound is 1-(2-chlorobenzoyl)-3-(3-chloro-4-(2-chloro-4-trifluoromethoxy-phenoxy)-phenyl]-urea of the formula

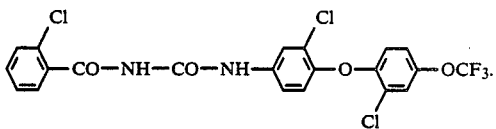

6. A compound according to claim 4, wherein such compound is 1-(2,6-difluorobenzoyl)-3-[3-chloro-4-(2-chloro-4-trifluoromethoxy-phenoxy)-phenyl]-urea of the formula

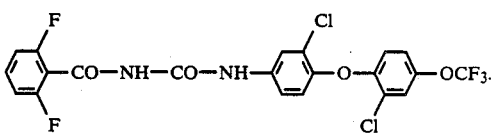

7. A compound according to claim 4, wherein such compound is 1(2,6-difluorobenzoyl)-3-[3,5-dimethyl-4-(3-chloro-4-trifluoromethoxy-phenoxy)-phenyl]-urea of the formula

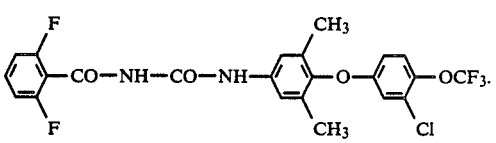

8. A compound according to claim 4, wherein such compound is 1-(2-chlorobenzoyl)-3-[3,5-dimethyl-4-(2-chloro-4-trifluoromethoxy-phenoxy)]-phenyl-urea of formula

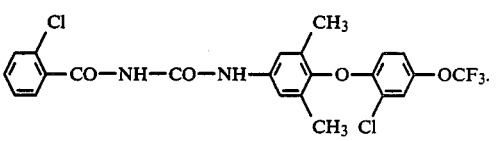

9. A compound according to claim 4, wherein such compound is 1-(2,6-difluorobenzoyl)-3-[3,5-diemthyl-4-(2-chloro-4-trifluoromethoxy-phenoxy)-phenyl]-urea of the formula

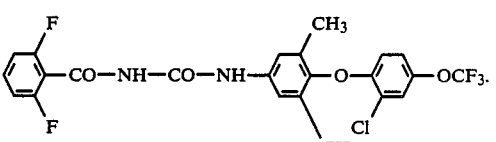

10. An insecticidal or acaricidal composition comprising an insecticidally or acaricidally effective amount of a compound according to claim 4 in admixture with a diluent.

11. A method of killing insects or acarids which comprises administering to such insects or acarids an insecticidally or acaricidally effective amount of a compound according to claim 4.

* * * * *

UNITED STATES PATENT AND TRADEMARK OFFICE
CERTIFICATE OF CORRECTION

PATENT NO. : 4,774,260
DATED : September 27, 1988
INVENTOR(S) : Wilhelm Sirrenberg, et al It is certified that error appears in the above-identified patent and that said Letters Patent is hereby corrected as shown below:

| | |
|---|---|
| Col. 4, line 3 | Correct --represent-- |
| Col. 8, line 4 | Delete "-" before "migratorioides" |
| Col. 9, line 52 | Delete "oorn" and substitute --corn- |
| Col. 12, line 2 | Before "20 ml" insert --approximately-- |
| Col. 15, lines 23, 32, 42 and 53 | Before "3" second instance insert --[-- |
| Col. 15, line 34 | After "of the" insert --formula-- |
| Col. 15, line 65 | Before "3" second instance delete "(" and substitute --[-- |
| Col. 16, line 35 | After "phenoxy)" delete "]" |
| Col. 16, line 35 | After "phenyl" insert --]-- |
| Col. 16, line 35 | After "of" insert --the-- |
| Col. 16, line 46 | Correct spelling of --dimethyl-- |

Signed and Sealed this

Eighth Day of August, 1989

Attest:

DONALD J. QUIGG

Attesting Officer

Commissioner of Patents and Trademarks